US009188553B2

(12) United States Patent
Sakuta et al.

(10) Patent No.: US 9,188,553 B2

(45) Date of Patent: Nov. 17, 2015

(54) X-RAY FLUORESCENCE ANALYZER

(71) Applicant: Hitachi High-Tech Science Corporation, Minato-ku, Tokyo (JP)

(72) Inventors: Masahiro Sakuta, Tokyo (JP); Kiyoshi Hasegawa, Tokyo (JP); Yoshiki Matoba, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 60 days.

(21) Appl. No.: 14/222,778

(22) Filed: Mar. 24, 2014

(65) Prior Publication Data

US 2014/0286474 A1 Sep. 25, 2014

(30) Foreign Application Priority Data

Mar. 25, 2013 (JP) ................................ 2013-061311

(51) Int. Cl.
*G01N 21/64* (2006.01)
*G01N 23/223* (2006.01)

(52) U.S. Cl.
CPC ........ *G01N 23/223* (2013.01); *G01N 2223/317* (2013.01); *G01N 2223/652* (2013.01)

(58) Field of Classification Search
CPC .......... G01N 23/223; G01N 2223/076; G01N 2223/301; G01N 23/2204
See application file for complete search history.

(56) References Cited

U.S. PATENT DOCUMENTS

| | | | | |
|---|---|---|---|---|
| 5,832,054 A * | 11/1998 | Kuwabara | ...................... | 378/45 |
| 2007/0211852 A1* | 9/2007 | Matoba | .......................... | 378/45 |

FOREIGN PATENT DOCUMENTS

| | | |
|---|---|---|
| JP | 2011-203102 A | 10/2011 |

* cited by examiner

*Primary Examiner* — Hoon Song
(74) *Attorney, Agent, or Firm* — Banner & Witcoff, Ltd.

(57) ABSTRACT

An X-ray fluorescence analyzer includes a sample stage having an opening at an X-ray irradiation position, an X-ray source which irradiates a sample placed on the opening with a primary X-ray from below, a detector which detects an X-ray fluorescence generated from the sample, a transparent drop prevention plate supported to be advanced and retracted immediately below the opening, a drive mechanism which advances and retracts the drop prevention plate, an observation camera which observes the drop prevention plate positioned immediately below the opening, and an operation unit which processes an image of the drop prevention plate which is captured by the observation camera. The operation unit detects a foreign matter on the drop prevention plate based on an image difference between images before and after the drive mechanism moves or vibrates the drop prevention plate within an observation range of the observation camera.

3 Claims, 3 Drawing Sheets

X-RAY FLUORESCENCE ANALYZER

CROSS-REFERENCE TO RELATED APPLICATION

This application claims priority from Japanese Patent Application No. 2013-061311, filed on Mar. 25, 2013, the entire subject matter of which is incorporated herein by reference.

TECHNICAL FIELD

The present invention relates to an X-ray fluorescence analyzer which is capable of, for example, detecting hazardous substances and is used for product screening or the like.

BACKGROUND

An X-ray fluorescent analysis is used for a qualitative analysis and a quantitative analysis of a sample by irradiating the sample with an X-ray emitted from an X-ray source, detecting an X-ray fluorescence which is a characteristic X-ray emitted from the sample by an X-ray detector, and then obtaining spectrums from the generated energy. The fluorescent X-ray analysis can be rapidly performed without destroying the sample, and thus widely used in a process and quality control or the like. In recent years, since a trace measurement can be performed with high-precision and high-sensitivity, the fluorescent X-ray analysis is expected to be used particularly as an analyzing method of detecting hazardous substances included in materials or composite electronic components.

A bottom-surface type apparatus which irradiates the sample with a primary X-ray from below is known as the X-ray fluorescence analyzer. Since a detector or the like is positioned below the sample, the bottom-surface type apparatus includes a transparent drop prevention plate disposed to a sample stage to prevent, for example, dropping a part of the sample when placing the sample. For example, JP-A-2011-203102 discloses an apparatus in which, while using a sample holder attached with a resin film such as a PET film called a Mylar film, a sample is put on the resin film, and the sample holder is placed to cover an opening of a base plate, and then, the sample is irradiated with an excited X-ray through the opening and the resin film.

SUMMARY

The above-described apparatus has the following problems.

That is, since the X-ray fluorescence analyzer irradiates the sample with an X-ray through the drop prevention plate, even a thin drop prevention plate absorbs the X-ray to some extent. Thus, it is preferable that the drop prevention plate not be used in X-ray irradiation. An apparatus including a drive mechanism which automatically retracts the drop prevention plate at the time of measurement has been proposed. However, there is a problem in that if the apparatus is driven in a state where the sample is dropped onto the drop prevention plate by accident, the sample is dropped from the drop prevention plate, which may cause a negative influence on an X-ray source, an analyzer, or the like disposed below, and the dropped sample may be lost.

The present invention has been made in view of the above-described circumstances, and an object of the present invention is to provide an X-ray fluorescence analyzer which is capable of detecting a foreign matter on a drop prevention plate.

According to an illustrative embodiment of the present invention, there is provided an X-ray fluorescence analyzer comprising: a sample stage which has an opening at an X-ray irradiation position and is configured to receive a sample placed on the opening; an X-ray source which is configured to irradiate the sample placed on the opening with a primary X-ray from below; a detector which is disposed below the opening and is configured to detect an X-ray fluorescence generated from the sample irradiated with the primary X-ray; a drop prevention plate which is transparent and supported to be advanced and retracted immediately below the opening; a drive mechanism which is configured to advance and retract the drop prevention plate; an observation camera which is disposed below the opening to observe the drop prevention plate when the drop prevention plate is positioned immediately below the opening; and an operation unit which is configured to process an image of the drop prevention plate which is captured by the observation camera, wherein the operation unit is configured to detect a foreign matter on the drop prevention plate based on an image difference between images before and after the drive mechanism moves or vibrates the drop prevention plate within an observation range of the observation camera.

According to the above X-ray fluorescence analyzer, the operation unit detects the foreign matter on the drop prevention plate based on the image difference between images before and after the drive mechanism moves or vibrates the drop prevention plate within the observation range of the observation camera. Accordingly, when the foreign matter is on the drop prevention plate, it is possible to detect the existence of the foreign matter by performing image processing with respect to the images before and after moving or vibrating the drop prevention plate in the operation unit and then obtaining the image difference. Therefore, even when the foreign matter of the sample or the like is dropped onto the drop prevention plate, it is possible to detect and remove the foreign matter before the drop prevention plate is completely retracted.

In the above X-ray fluorescence analyzer, the operation unit may be configured to obtain the image difference in accordance with a direction of the drop prevention plate moved or vibrated by the drive mechanism.

According to this configuration, since the operation unit obtains the image difference in accordance with a direction of the drop prevention plate moved or vibrated by the drive mechanism, it is possible to accurately detect the existence of the foreign matter through the simple image processing.

The above X-ray fluorescence analyzer may further comprise: a brush portion which is disposed at a position away from immediately below the opening and is configured to drop a foreign matter on an upper surface of the drop prevention plate while contacting the upper surface of the drop prevention plate being moved when the drop prevention plate is retracted; and a foreign matter receiving portion which is disposed immediately below the brush portion and is configured to receive a foreign matter dropped from the drop prevention plate by the brush portion.

According to this configuration, it is possible to automatically remove the foreign matter dropped from the drop prevention plate at the time of retraction and receive the foreign matter in the foreign matter receiving portion without affecting the X-ray source or the detector disposed below.

According to the above configuration, the following effects may be obtained.

According to the above-described X-ray fluorescence analyzer, the operation unit detects the foreign matter on the drop prevention plate based on the image difference between images before and after the drive mechanism moves or vibrates the drop prevention plate within the observation range of the observation camera. Accordingly, even when the foreign matter such as the sample is dropped onto the drop prevention plate, it is possible to detect and remove the foreign matter before the drop prevention plate is retracted. Therefore, in the X-ray fluorescence analyzer, by detecting and removing the foreign matter before measurement, there may be no concern that the foreign matter is dropped in the vicinity of the X-ray source or the detector, or the foreign matter enters gaps. Accordingly, the stable measurement of the product screening or the like in view of the regulation on certain hazardous substances can be performed.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Hereinafter, an X-ray fluorescence analyzer according to illustrative embodiments of the present invention will be described with reference to FIGS. 1 to 4B.

Figure 1:
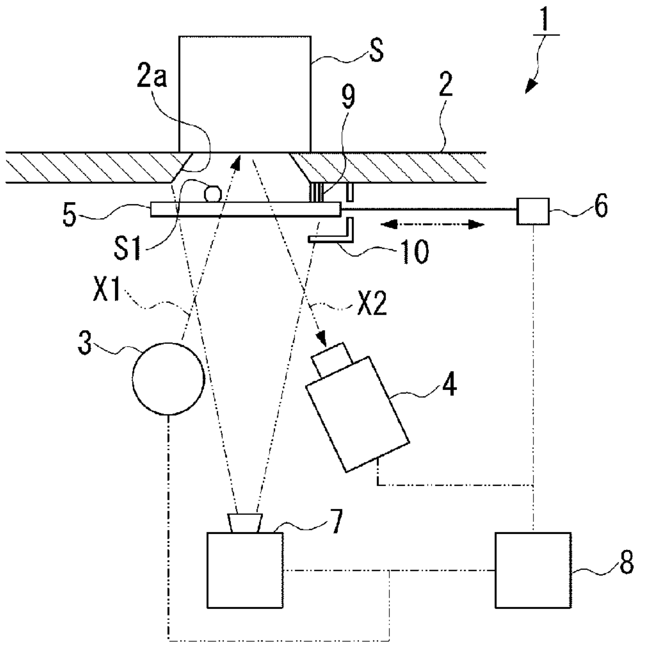
FIG. 1 is a view showing an overall schematic configuration which has a portion partially cross-sectioned in an X-ray fluorescence analyzer according to an illustrative embodiment of the present invention.

As shown in FIG. 1, an X-ray fluorescence analyzer 1 of the illustrative embodiment includes a sample stage 2 which has openings 2*a* at a X-ray irradiation position and can place a sample S on each of the openings 2*a*, an X-ray source 3 which irradiates the sample S placed on the opening 2*a* with a primary X-ray X1 from below, and a detector 4 which is disposed at the lower side with respect to the opening 2*a* and detects an X-ray fluorescence X2 generated from the sample S which is irradiated with the primary X-ray X1.

The X-ray fluorescence analyzer 1 further includes a drop prevention plate 5 which is transparent and supported to be advanced and retracted immediately below the opening 2*a*, a drive mechanism 6 which advances and retracts the drop prevention plate 5, an observation camera 7 which is disposed below the opening 2*a* to observe the drop prevention plate 5 when the drop prevention plate 5 is positioned immediately below the opening 2*a*, and an operation unit 8 which processes an image of the drop prevention plate 5 which is captured by the observation camera 7.

Figure 2:
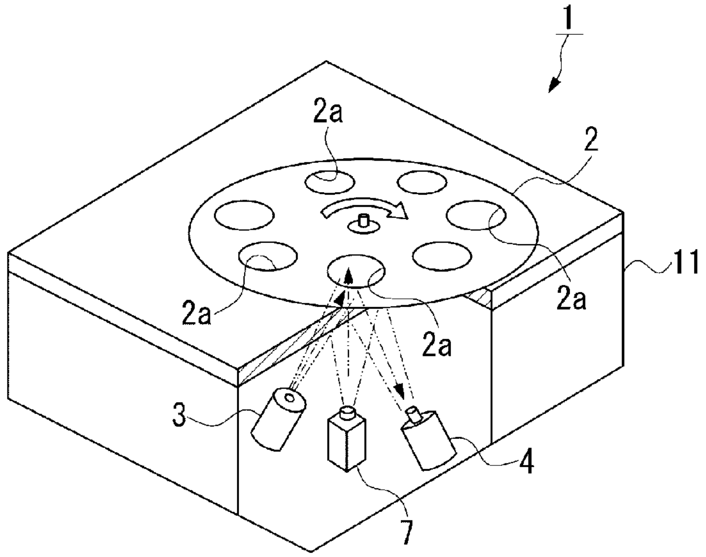
FIG. 2 is a schematic perspective view, which has a portion partially cut away, showing the X-ray fluorescence analyzer according to the illustrative embodiment.

The sample stage 2 is a rotatable sample changer which is rotatably supported on a housing 11 of the apparatus and has a plurality of openings 2*a*, and is rotationally driven by a rotation mechanism (not illustrated) such as a motor provided inside the housing 11 as shown in FIG. 2.

Further, the X-ray source 3, the detector 4, and the observation camera 7 are accommodated inside the housing 11.

The drive mechanism 6 is a motor or the like which is connected to the drop prevention plate 5 and can advance and retract the drop prevention plate 5, and can horizontally move the drop prevention plate 5 to any position in a range from immediately below the opening 2*a* to the retracted position or can provide vibration to the drop prevention plate 5 being moved by a short distance at an accelerated rate.

The drive mechanism 6 includes a brush portion 9 which is disposed at a position away from immediately below the opening 2*a* and drops the foreign matter S1 on an upper surface of the drop prevention plate 5 by contacting the upper surface of the drop prevention plate 5 being moved when the drop prevention plate 5 is retracted, and a foreign matter receiving portion 10 which is disposed immediately below the brush portion 9 and receives the foreign matter S1 dropped from the drop prevention plate 5 by the brush portion 9.

The drop prevention plate 5 is formed of a transparent resin plate made of a PET film called a Mylar film, for example.

The brush portion 9 is attached to a lower surface of the sample stage 2 at a periphery of the opening 2*a* in a state of protruding downward.

The foreign matter receiving portion 10 has an upper portion attached on a lower surface of the sample stage 2 and is disposed below the drop prevention plate 5 at the retracted position such that the drop prevention plate 5 can be advanced or retracted.

The X-ray source 3 is an X-ray tube capable of emitting a primary X-ray. Specifically, the X-ray source 3 emits from a window such as a beryllium foil, as the primary X-ray X1, an X-ray which is generated by collision of thermo electrons generated from a filament (cathode) inside the tube and accelerated by a voltage applied between the filament (cathode) and a target (anode), with W (tungsten), Mo (molybdenum), and Cr (chromium) of the target.

The detector 4 includes a semiconductor detecting element (for example, Si (silicon) element which is pin structure diode) (not illustrated) disposed in an incident window of the X-ray, and when one X-ray photon is incident thereon, a current pulse corresponding to the one X-ray photon is generated. An instant current value of the current pulse is in proportion to the incident characteristic X-ray energy. The detector 4 is set such that the current pulse generated from the semiconductor detecting element is converted into the voltage pulse, amplified and output as a signal.

The observation camera 7 is a charge-coupled device (CCD) capable of capturing the upper part of the drop prevention plate 5 through the transparent drop prevention plate 5. The observation camera 7 has a function of sending image data of the captured upper part of the drop prevention plate 5 to the operation unit 8.

The operation unit 8 has a function of detecting the foreign matter S1 on the drop prevention plate 5 based on an image difference between images before and after the drive mechanism 6 moves or vibrates the drop prevention plate 5 within the observation range of the observation camera 7. The operation unit 8 performs a process of obtaining the image difference in accordance with the direction of the drop prevention plate 5 moved or vibrated by the drive mechanism 6. That is, a differential process of two images is performed by calculating a correlation coefficient corresponding to the direction of the drop prevention plate 5 moved or vibrated.

The operation unit 8 is a computer which is connected to the X-ray source 3, the detector 4, the observation camera 7, and the rotating mechanism of the sample stage 2, and has, for example, a CPU as a control unit functioning of controlling the above connected components. The operation unit 8 has a display for displaying various pieces of information (not illustrated) and is disposed outside the housing 11. The operation unit 8 controls the start of measurement with a measurement start button (not illustrated).

The X-ray fluorescence analyzer 1 of the illustrative embodiment includes an analyzer (not illustrated) which is connected to the detector 4 and analyses a signal from the detector 4. The analyzer is a pulse-height analyzer (multi-channel pulse height analyzer) which generates an energy spectrum by obtaining a pulse height value of pulse voltage from the above-descried signal.

Next, an X-ray analysis method by using an X-ray analyzer of the illustrative embodiment will be described with reference to FIGS. 1 to 4B.

Figure 3A:
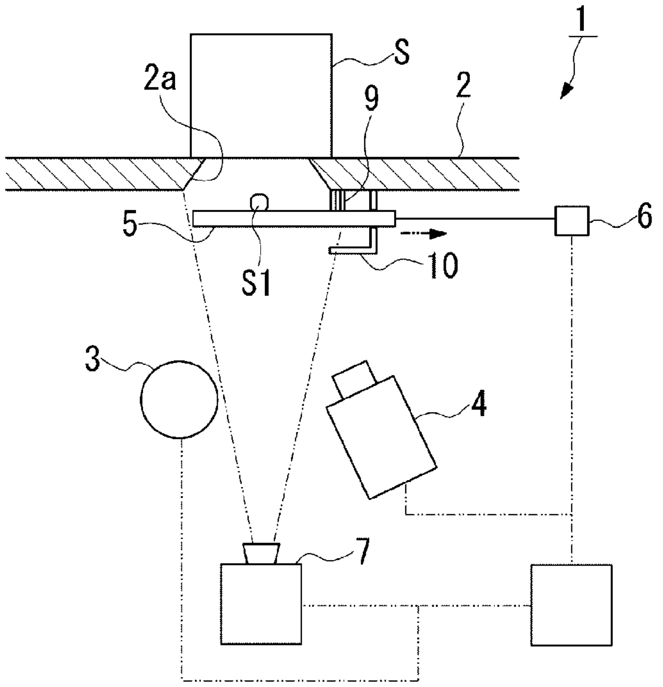
FIGS. 3A and 3B are views showing a schematic overall configuration showing a state after a drop prevention plate is moved, and a state where the drop prevention plate is retracted when a foreign matter is detected according to the illustrative embodiment.
Figure 4A:
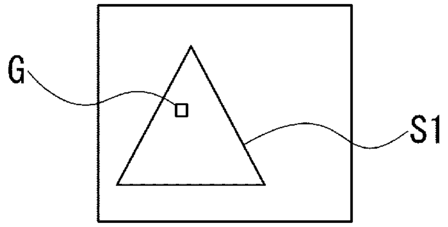
FIGS. 4A and 4B are an explanatory views showing an image before the drop prevention plate is moved and an image after the drop prevention plate is moved when the foreign matter is detected according to the illustrative embodiment.

First, as shown in FIG. 1, the sample S is set to cover the opening 2*a* on the sample stage 2. At this time, the drive mechanism 6 moves the drop prevention plate 5 to position immediately below the opening 2*a*. In this state, when a measurer presses the measurement start button, the observation camera 7 captures the drop prevention plate 5 and sends the captured image data to the operation unit 8 as shown in FIG. 4A. Next, as shown in FIG. 3A, the operation unit 8 controls the drive mechanism 6 to move the drop prevention plate 5 by 0.5 mm. Then, the observation camera 7 captures the drop prevention plate 5 again, and sends the captured image data as shown in FIG. 4B to the operation unit 8.

Subsequently, the operation unit 8 performs the image processing of the images (FIGS. 4A and 4B) before and after the movements in accordance with the moving directions and then calculates the image difference. The operation unit 8 determines that the foreign matter S1 of the sample S or the like is not dropped when the obtained image difference value is less than a threshold value set in advanced. In this case, the operation unit 8 performs the X-ray analysis after moving the drop prevention plate to the retracted position by the drive mechanism 6.

The operation unit 8 determines that the foreign matter S1 of the sample S or the like is dropped when the obtained image difference value is equal to or greater than the threshold value set in advanced. In this case, the operation unit 8 displays the existence of the foreign matter S1 on the display to the measurer after returning to an initial state and stopping the operation.

Figure 4B:
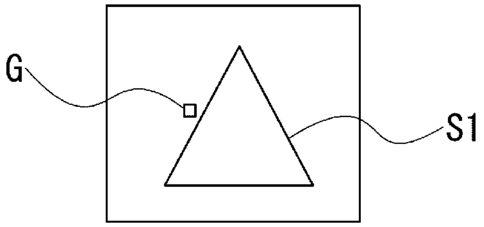

That is, when comparing the images before and after the movement with each other, if the foreign matter S1 exists, the foreign matter S1 is moved in the movement direction by a moving distance of the drop prevention plate 5 while a position of a pixel G is not changed, as shown in FIGS. 4A and 4B. Accordingly, the image data in the same pixel G is changed, and thus, even in the entire image, the image difference before and after the movement is generated in accordance with size and quantity of the foreign matter S1. In this way, by calculating the image difference between images before and after the movement in accordance with the movement direction through the image processing, the foreign matter S1 dropped onto the drop prevention plate 5 can be detected.

Incidentally, in the above-described foreign matter detection method, the existence of the foreign matter S1 is determined by the image difference between images before and after the movement when the drop prevention plate 5 is slightly moved by the drive mechanism 6. However, the operation unit 8 may vibrate the drop prevention plate 5 with the drive mechanism 6 which rapidly moves the drop prevention plate 5 by a short distance at an accelerated rate and stops the movement, and move the foreign matter S1 on the drop prevention plate 5 with respect to the drop prevention plate 5 due to the vibration. In this case, the operation unit 8 may determine the existence of the foreign matter S1 from the difference between images before and after the vibration.

When the foreign matter S1 is detected as described above, the measurer can perform the measurement again by removing the foreign matter S1 on the drop prevention plate 5.

Figure 3B:
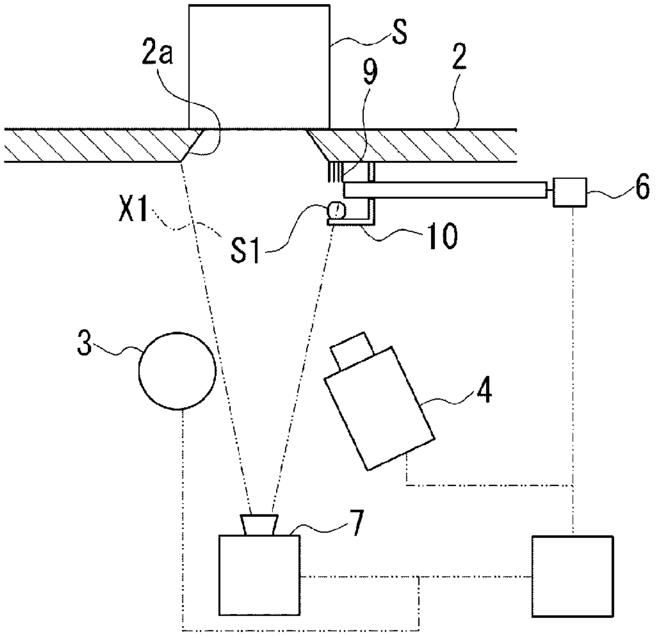

Further, in the X-ray fluorescence analyzer 1 of the illustrative embodiment, in a case where the measurer does not remove the foreign matter S1 by hand or the foreign matter S1 is a small amount or is small in size, when the drop prevention plate 5 having the foreign matter S1 thereon is moved to the retracted position by the drive mechanism 6, the foreign matter S1 which comes into contact with the brush portion 9 is pressed by the brush portion 9 and is moved on the drop prevention plate 5 at the time of the movement. Accordingly, the foreign matter S1 is dropped onto the foreign matter receiving portion 10 from the end of the drop prevention plate 5, as shown in FIG. 3B. Therefore, it is possible to automatically remove the foreign matter S1 from the drop prevention plate 5 without the measurer removing the foreign matter S1.

Incidentally, as for the measurement, it is necessary to close a sample door (not illustrated) of the apparatus after placing the sample S so that the X-ray is shielded. However, when the measurement start button is pressed after closing the sample door and then the drop prevention plate 5 is moved, there is concern that the procedure is performed in series and thereby the measuring time may be prolonged. For this reason, by automatically performing the operations of the sample door and the drop prevention plate 5 at the same time, it is preferable that the procedure be performed in parallel in order to shorten the measuring time. That is, it is possible to shorten the measuring time after pressing the measurement start button by controlling the operation unit 8 to detect the image difference in response to a switch when closing the sample door.

Further, in a case where the consecutive measurement is performed by setting a plurality of samples S on the sample stage 2 which is the rotatable sample changer, there is concern that some of the plurality of the samples S are dropped onto the drop prevention plate 5 each time the sample stage 2 is rotated, and thus it is preferable to set the foreign matter S1 to be detected at each of the rotations.

As described above, in the X-ray fluorescence analyzer 1 of the illustrative embodiment, the operation unit 8 detects the foreign matter S1 on the drop prevention plate 5 based on the image difference between images before and after the drive mechanism 6 moves or vibrates the drop prevention plate 5 within the observation range of the observation camera 7. Accordingly, when the foreign matter S1 is on the drop prevention plate 5, it is possible to detect the existence of the foreign matter S1 by performing image processing with respect to the images before and after moving or vibrating the drop prevention plate 5 in the operation unit 8 and to obtain the image difference. Therefore, even though the foreign matter S1 such as the sample S is dropped onto the drop prevention plate 5, the foreign matter S1 can be detected and removed before retracting the drop prevention plate 5.

Further, the operation unit 8 may obtain the image difference in accordance with the direction of the drop prevention plate 5 moved or vibrated by the drive mechanism 6, and thus accurately detect the existence of the foreign matter S1 through the simple image processing.

Further, the X-ray fluorescence analyzer 1 includes the brush portion 9 which drops the foreign matter S1 on the upper surface of the drop prevention plate 5 when the drop prevention plate 5 is retracted, and the foreign matter receiving portion 10 which receives the foreign matter S1 dropped from the drop prevention plate 5 by the brush portion 9. Accordingly, it is possible to automatically remove the foreign matter S1 dropped from the drop prevention plate 5 at the time of retraction and receive the foreign matter S1 in the foreign matter receiving portion 10 without affecting the X-ray source 3 or the detector 4 disposed below.

While the present invention has been shown and described with reference to certain illustrative embodiments thereof, it will be understood by those skilled in the art that various changes in form and details may be made therein without departing from the spirit and scope of the invention as defined by the appended claims.

For example, the energy dispersion type X-ray fluorescence analyzer which measures the X-ray energy and intensity by using the pulse-height analyzer is employed in the above-described illustrative embodiment. However, a wavelength dispersion type of X-ray fluorescence analyzer which disperses the X-ray fluorescence by spectral crystal and measures the wavelength and intensity of the X-ray may be employed.

What is claimed is:

1. An X-ray fluorescence analyzer comprising:

a sample stage which has an opening at an X-ray irradiation position and is configured to receive a sample placed on the opening;

an X-ray source which is configured to irradiate the sample placed on the opening with a primary X-ray from below;

a detector which is disposed below the opening and is configured to detect an X-ray fluorescence generated from the sample irradiated with the primary X-ray;

a drop prevention plate which is transparent and supported to be advanced and retracted immediately below the opening;

a drive mechanism which is configured to advance and retract the drop prevention plate;

an observation camera which is disposed below the opening to observe the drop prevention plate when the drop prevention plate is positioned immediately below the opening; and an operation unit which is configured to process an image of the drop prevention plate which is captured by the observation camera, wherein the operation unit is configured to detect a foreign matter on the drop prevention plate based on an image difference between images before and after the drive mechanism moves or vibrates the drop prevention plate within an observation range of the observation camera.

2. The X-ray fluorescence analyzer according to claim 1, wherein the operation unit is configured to obtain the image difference in accordance with a direction of the drop prevention plate moved or vibrated by the drive mechanism.

3. The X-ray fluorescence analyzer according to claim 1, further comprising:

a brush portion which is disposed at a position away from immediately below the opening and is configured to drop a foreign matter on an upper surface of the drop prevention plate while contacting the upper surface of the drop prevention plate being moved when the drop prevention plate is retracted; and a foreign matter receiving portion which is disposed immediately below the brush portion and is configured to receive a foreign matter dropped from the drop prevention plate by the brush portion.

* * * * *